United States Patent [19]

Cohen

[11] 4,137,917

[45] Feb. 6, 1979

[54] SYRINGE FILTER UNIT

[76] Inventor: Milton J. Cohen, 9201 Persimmon Tree Rd., Potomac, Md. 20854

[21] Appl. No.: 783,480

[22] Filed: May 12, 1977

[51] Int. Cl.² ............................................. A61M 5/00
[52] U.S. Cl. ................................. 128/218 R; 128/221
[58] Field of Search ........ 128/218 R, 218 N, 218 NV, 128/218 M, 220, 221, 215, 272.3, 272.1, 234, 214 F; 210/232, 322, 323, 340, 341, 447

[56] References Cited

U.S. PATENT DOCUMENTS

| 963,324 | 7/1910 | Randall | 210/323 T |
|---|---|---|---|
| 3,640,277 | 2/1972 | Adelberg | 128/214 F |
| 3,757,780 | 9/1973 | Ishikawa | 128/221 |
| 4,008,718 | 2/1977 | Pitesky | 128/272.3 |

Primary Examiner—John D. Yasko
Attorney, Agent, or Firm—McDougall, Hersh & Scott

[57] ABSTRACT

A syringe filter unit, said unit attachable to the hub of any hypodermic syringe, the unit forming a housing, in which is incorporated, a displaceable filter or filters, said filters capable of filtering air, or a liquid, into or out of a syringe, said filter capable of being used in an infusion device, or other similarly used equipment, i.e. trans-fusion device, said filter also capable of being used in the filtering of wines, or other solutions manufactured commercially.

7 Claims, 9 Drawing Figures

U.S. Patent    Feb. 6, 1979    Sheet 1 of 2    4,137,917
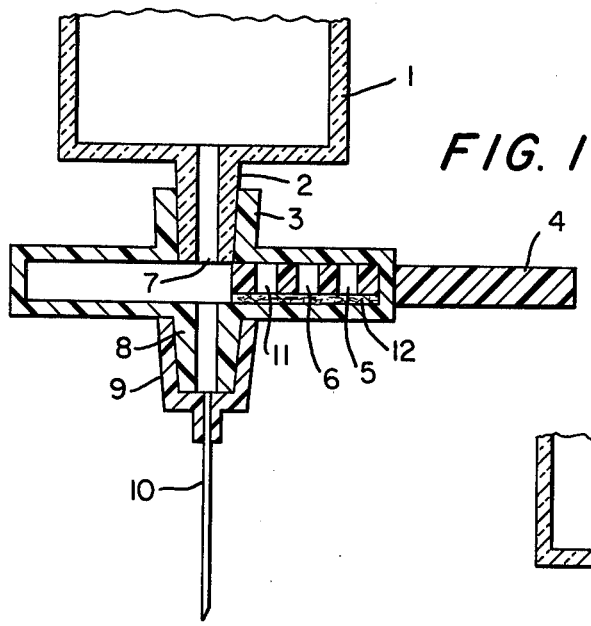
FIG. 1
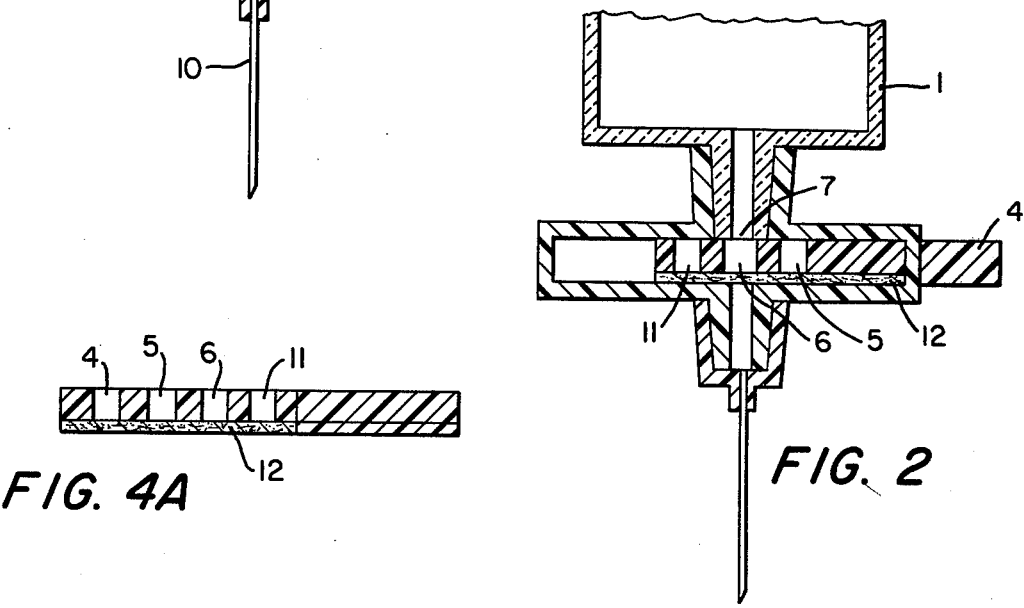
FIG. 4A
FIG. 2
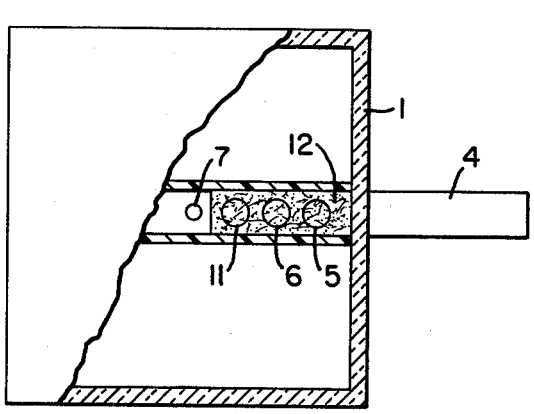
FIG. 3
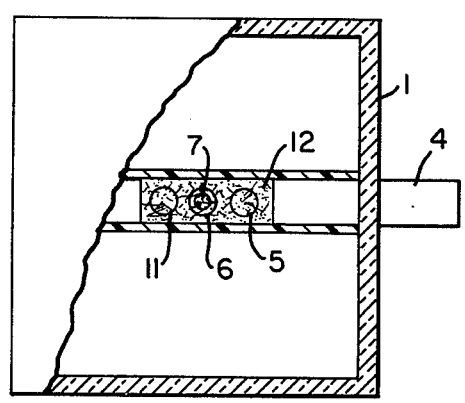
FIG. 4

SYRINGE FILTER UNIT

In the use of parenteral solutions, the method most used, is to use a disposeable syringe, with a disposeable needle, said needle being inserted through a rubber stopper, into a vial of liquid medication. Air, from the barrel, is forced into the vial, the plunger pulled back, and the solution is drawn back into the barrel, the needle withdrawn from the vial, after which said needle is inserted into a patient, the solution injected, the needle withdrawn, and the syringe and needle discarded.

Also, many solutions must be made at the time of use, since such solutions in storage, would lose their efficacy. To overcome this aspect, at present, two vials, one with a liquid, and one with the dry medications, is employed, a syringe being first introduced into the liquid vial, withdrawn, as described above, and the needle reinserted into the vial of dry medication, wherein the liquid merges with the dry material, to form a mixed solution, after which the mixed solution is withdrawn, and injected in a patient, the syringe discarded, etcetera.

In the case of the one vial, the air injected into the vial, in order for the liquid to be able to be withdrawn, is contaminated air, since it is room air, and contains bacteria from the persons in that room, breathing, coughing, sneezing, smoking, plus that that material sent into the air from the contamination by shoes from the outside, as the rug or floor is walked on. Besides this, the needle going through the rubber, may core out tiny particles of rubber, which could be incorporated into the solution, plus the solution itself could contain particulate matter, pyrogens, etcetera, so that when the solution is brought back into the barrel, it could be contaminated in several ways.

In the case of the making of an immediate solution, the contamination is magnified, since two vials are used for the end solution, so that the above described steps to place a solution into a syringe, are doubled, with all of the misgivings compounded.

Therefore; it is a prime object of this invention to overcome all of the negatives mentioned in the foregoing written material.

Another object, is to present means of providing a solution for injection, that is definitely sterile, as much as could be humanly possible.

Another object, is to provide an attachable hub, for doing the above, that is simple in construction, assembly and use, and of course, inexpensive to produce.

Another object, is to provide an incorporated series of filters, the number of same depending upon the particular use, within said hub, to accomplish the purpose intended.

Another object, of the invention, is to provide the means mentioned above, said means being able to be used on any empty, unpackaged, syringe, not having a needle permanently attached to the hub, to the hub of the syringe itself.

These and other objects and advantages of this invention, will hereinafter appear, and for purposes of illustration, but not of limitation, embodiments of the invention as shown in the accompanying drawings, in which:

In FIG. 1, there is a schematic cross section of the device, sidewise, showing all parts involved ready for actuation of same.

In FIG. 2, actuation has been accomplished, with the device performing its purpose.

In FIG. 3, is a view of the device looking up toward the barrel, prior to actuation.

In FIG. 4, the device has been actuated, and performing its purpose.

FIG. 4A, is a cross section of the filter unit.

Figure 5:
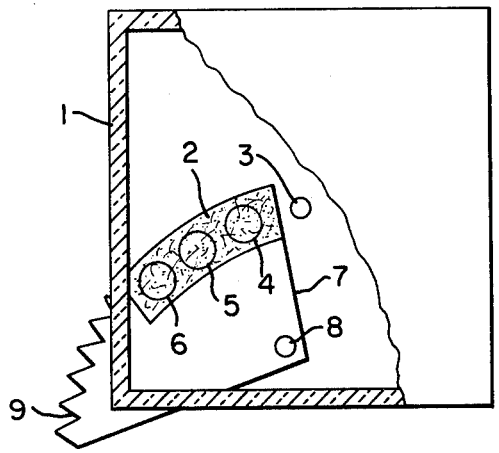
FIGS. 5 through 8, show a modification of the filter in a rotatable dial form.

Now, in FIG. 1, there is present a syringe barrel 1, having attached to its hub, a combination needle hub and filtering means assembly, the upper surface of same having an outward projection 3, which is the means of attaching said assembly to the hub of the syringe, the lower surface of same, having an outward projection 8, to which is attached a needle hub 9, said hub having a needle 10 embedded in same. Lying within these surfaces of the aforedescribed means, lies a moveable slab of plastic material, 4, said slab having at its inner end, three passages, 5, 6, and 11, the bottom of said passages being covered by a filter 12, the outer portion of said slab lying outside of the assembly, for grip by the fingers of the user. The center of the assembly, is set so that there is a continuous passageway from the hub 7, through said assembly, through the needle hub, and through the needle.

In FIG. 2, actuation has begun, with the moveable slab 4 having been pushed inwardly by finger action on the outer area of said slab, resulting in a lining up of the first passageway 11, and then the second passageway 6, as shown, and finally the third passageway 5, each in turn being in the way of the passageways between the two hubs 3 and 9 just described. With this lin-ng up, the adjacent filter 12, has in turn been lined up with the aforementioned passageways 5, 6 and 11.

In FIG. 3, is the view looking up on the passageways 5, 6 or 11, through the body of the filter 12, before actuation.

In FIG. 4, one can see the passageway of the slab 4 and its accompanying filter 12 lined up with the passageway of the hub to hub area, the slab 4 having been pushed inwardly so that said lining up of passageways to passageways, could be accomplished, with the particular passageway 6 and its accompanying filter 12, showing in direct line with the hub to hub passageways.

In use, one could use this innovative hub unit, on any empty syringe, plastic or glass, which does not have a permanently attached needle to h its barrel hub. The unit is attached to the hub 2 of a syringe. Before actuation, the filters 5, 6 and 11, with the accompanying filter slabe 4, are in position, out of line with the opening in the syringe hub 7. To actuate, one first pushes the filter units inwardly by finger pressure on the slab 4, so that filter 11 is in direct line with the hub opening 7. The needle is inserted through the rubber stopper of the vial, and the syringe plunger is pushed downwardly all the way down the barrel. This action causes the entrapped air within the barrel, to be forced into the vial, through filter 11. Once this is done, the filter unit is again pushed one notch further inwardly, which removes the filter 11 away from the hub opening 7, and allows the filter 6 to be placed in line with the hub opening 7. The syringe plunger is now drawn back upwardly within the barrel all the way. This action, causes liquid in the vial to be drawn into the barrel and through the filter. Once the barrel is filled, again the filter unit is pushed inwardly a notch, displacing the filter 6, and placing the filter 5 in line with the opening 7 in the hub. The needle is removed from the vial, and inserted into the patient. The plunger in the syringe is again forced downwardly in the barrel all of its length. This action causes the liquid to be forced through the last filter 5, into the patient. The needle is removed from the patient, and the entire syringe and needle is discarded.

In the case of the use of two vials, for the making of a definite fresh mix at the time of use, the needle of the syringe is placed through the rubber seal of the liquid vial, after which the plunger is pushed downwardly all of the way, in the barrel. This causes the entrapped air in the syringe to be forced into the vial through the filter 11. The filter unit is pushed inwardly again, filter 11 being displaced by filter 6, after which the plunger is retracted up the barrel, said action causing the liquid to enter and fill the barrel. The filter unit is again pushed inwardly, filter 6 being displaced by filter 5. The syringe needle is removed from the vial liquid, and reinserted into the vial of the dry medication, the plunger being again pushed downwardly, causing the liquid to enter the dry vial through the filter 5, where it mixes with the dry material to form a new solution. Filter 5 is replaced by filter 6, after which the mixed solution is redrawn back up into the barrel through filter 6; the needle is withdrawn from the vial, inserted into the patient, after which the liquid mix passes through 11 to enter the patient. Once the syringe is empty, it is removed from the patient and discarded.

It is obvious here, that this is an ultra method of assuring the injection of a sterile prepared solution from the one vial, or a sterile solution, made at the time of mix, into a patient. In the case of the prepared solution, filters completely filter first the air going into the solution, secondly the solution being drawn into the syringe is filtered, and finally, the solution in the syringe, is doubly filtered, in that it passes through a third filter, on its way into the patient. In the case of the mix at time of use, the air is filtered as it enters the vial of liquid, the liquid being drawn back into the syringe is filtered, pushing the filtered liquid into the dry vial, also filters that liquid again, and drawing up the mix of liquid and dry material also passes through a filter, and finally, the new mix as it enters the patient, is again filtered.

There is a modification of the invention presented in FIGS. 5 through 8. Instead of using a push-through slab effect to change the position of the different filters, a dial effect is used to move the filters into their eventual positions. Viewing the filter hub from below, towards the barrel, in FIG. 5 there is present a hub 1, and anchored near the inside of the bottom of same, is the rotatable dial 7, held in moveable position by a post 8, said dial being somewhat shaped like a portion of a circle, and having along its outer edge, three filters, 4, 5 and 6, all lying in the path of the exit end 3 of a syringe hub 10. The outer exposed edge of the dial, is serrated to prevent slippage of the finger, as said finger exerts pressure on the dial for rotating same.

Figure 6:
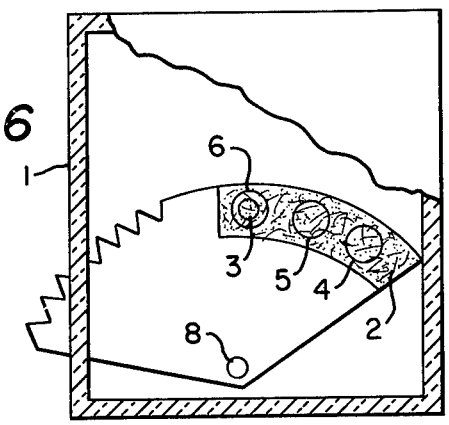

In FIG. 6, the hub has been actuated, and shown here, filter 6 has been positioned over the exit end of the syringe barrel, which would be followed by filter 5 and 4, as the hub is being completely used, the actions for the results intended being the same basically, as in the first version of the device.

Figure 7:
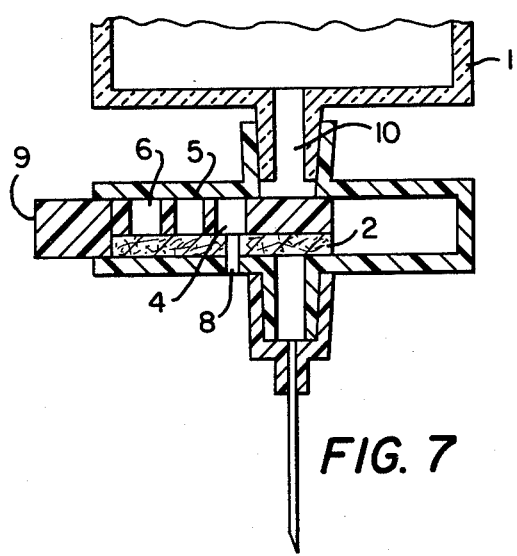

In FIG. 7, a cross-section view is shown, with none of the filters having been pushed into place for respective actions.

Figure 8:
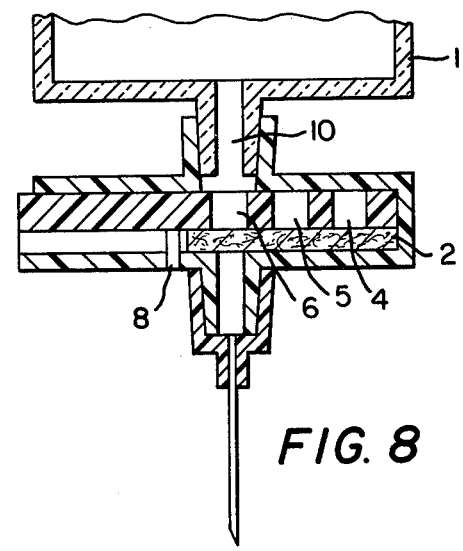

In FIG. 8, the cross-section view shows the device actuated, with filter 6 in position over the syringe hub exit 3, for the beginning of the use of the hub.

It is to be noted, that not only does this invention apply to the use of parenteral medications, via a hypodermic syringe, but also particularly to that type of equipment and accories, which are employed for the purpose of the injecting of intravenous medication of all types, for use in equipment and accessories employed for transfusion purposes, (blood exchange between patients, patient feeding, where the food is unable to be taken by mouth and absorbed through the intestinal tract, for the intravenous infusion of different types of drugs which are used for diagnostic purposes, such as for X-ray contract media, nuclear material material, etcetera.)

It will be understood, that changes may be made, in the details of construction, arrangement, and operation, without departing from the spirit of the invention, especially as defined in the following claims.

I claim:

1. A multiple filter assembly for use with hypodermic syringes or similar devices comprising:
    (a) a filter hub adapted to be interposed between the hub and opening of said syringe and a needle hub, said filter hub including a passageway communicating said syringe opening with the needle hub,
    (b) a member movably attached to said filter hub positionable in blocking relation across said passageway, said member having at least two openings therethrough, each of which when positioned in said passageway, permits communication between said syringe opening and said needle hub via said passageway,
    (c) filter means carried by said movable member immediately adjacent said openings,
    whereby during the transfer of medicaments into and out of the syringe during preparation and injection, a different one of said openings is positioned in said passageway to insure that foreign materials do not enter the syringe nor are they subsequently injected during discharge of the medicament from the syringe.

2. The filter assembly according to claim 1 wherein said filter hub defines an enclosure and said filter means is retained therein regardless of the position of said movable member to prevent contamination.

3. The filter assembly according to claim 1 wherein said movable member is an elongated rectangular slab and sequential positioning of said openings is effected by progressive insertion of said slab into said filter hub.

4. The filter assembly according to claim 1 wherein said movable member is a semi-circular disk and sequential positioning of said openings is effected by progressive rotation of said disk.

5. The filter assembly according to claim 1 wherein said filter means is a filter element disposed on the needle hub side of said openings through said movable member.

6. A method of filtering and preparing medicaments prior to injection with a hypodermic syringe comprising the steps of:
    (a) positioning a first filter unit over the syringe hub opening,
    (b) drawing the medicament into the syringe in the conventional manner through said first filter,
    (c) positioning a second filter unit over the syringe hub opening,
    (d) dispensing the medicament in the syringe via said hub opening through said second filter, (e) repeating steps (a) through (d) with additional filters as often as necessary to complete the preparation of the medicament and effect injection.

7. The method according to claim 6 wherein the medicament is formed of a dry component and a liquid component which must be mixed together prior to injection and steps (a) to (d) are performed once to filter and receive the liquid component and inject it into the dry component and once again to filter and receive the mixed components and inject the mixture, four filter units being employed for the method.

* * * * *